(12) United States Patent
Karlsen

(10) Patent No.: US 6,723,505 B1
(45) Date of Patent: Apr. 20, 2004

(54) METHOD FOR IDENTIFICATION OF THE INDICATORS OF CONTAMINATION IN LIQUID SAMPLES

(75) Inventor: Frank Karlsen, Klokkarstua (NO)

(73) Assignee: Nye Colifast AS

(*) Notice: Subject to any disclaimer, the term of this patent is extended or adjusted under 35 U.S.C. 154(b) by 232 days.

(21) Appl. No.: 09/634,960

(22) Filed: Aug. 8, 2000

Related U.S. Application Data

(60) Provisional application No. 60/149,365, filed on Aug. 13, 1999.

(51) Int. Cl.$^7$ .................... C12Q 1/68; C12P 19/34; C07H 21/04
(52) U.S. Cl. .................... 435/6; 435/91.2; 536/23.1; 536/24.3; 536/24.32
(58) Field of Search .................... 435/6, 91.2; 536/23.1, 536/24.3, 24.32; 436/63, 94

(56) References Cited

U.S. PATENT DOCUMENTS

| | | | | |
|---|---|---|---|---|
| 5,292,644 A | | 3/1994 | Berg ........................... | 435/29 |
| 5,298,392 A | * | 3/1994 | Atlas et al. .................. | 435/6 |
| 5,518,894 A | | 5/1996 | Berg ........................... | 435/34 |
| 5,541,308 A | | 7/1996 | Hogan et al. ............... | 536/23.1 |
| 5,824,557 A | | 10/1998 | Burke et al. ................. | 436/94 |

FOREIGN PATENT DOCUMENTS

| | | | | |
|---|---|---|---|---|
| WO | WO 93/10263 | * | 5/1993 | .................... 435/6 |

OTHER PUBLICATIONS

Handbook of Fluorescent Probes and Research Chemicals (Molecular Probes), 6th ed. 1996, pp 161–162.*
Biosystems Reporter, vol. II, issue 28, 1996, pp 1–3.*
Clement, Jean Marie et al., "Gene Sequence of the λReceptor, an Outer Membrane Protein of *E. coli* K12", Cell, vol. 27, 507–514, Dec. 1981 (Part 2).
"First Automated PCR–Based System for the Detection of Salmonella in Food", *Biosystems Reporter*, 28(II):1–3, 1996.
Jensen, L.B. Internal Size Variations in Tn1546 like elements due to the presence of IS1216V. FEMS Microbiology Letters. 1998, vol. 169, pp. 349–354.
PCT Transmittal of the International Search Report, Dated Jan. 23, 2001.

* cited by examiner

*Primary Examiner*—Jehanne Souaya
(74) *Attorney, Agent, or Firm*—Dunlap, Codding & Rogers, P.C.

(57) ABSTRACT

A method for the identification of the presence of *E. coli,* and *Enterococcus faecalis* and/or *Enterococcus faecium* in liquid or liquified samples. The method employs novel oligonucleotide primers based on sequences of the *E. coli* LamB gene and the *Enterococcus faecalis/faecium* transposase gene Tn1546. The method involves enrichment of the liquid or liquified sample, preferably using a selective medium, obtaining DNA from bacteria in the sample, and PCR amplification of the DNA using the novel oligonucleotide primers. Kits with the primers are also contemplated.

25 Claims, No Drawings

SEQUENCE LISTING

<160> NUMBER OF SEQ ID NOS: 38

<210> SEQ ID NO 1
<211> LENGTH: 24
<212> TYPE: DNA
<213> ORGANISM: Escherichia coli

<400> SEQUENCE: 1
gtaaagggct gtcgcagggt tctg                                              24

<210> SEQ ID NO 2
<211> LENGTH: 23
<212> TYPE: DNA
<213> ORGANISM: Escherichia coli

<400> SEQUENCE: 2
taaagggctg tcgcagggtt ctg                                               23

<210> SEQ ID NO 3
<211> LENGTH: 23
<212> TYPE: DNA
<213> ORGANISM: Escherichia coli

<400> SEQUENCE: 3
gtaaagggct gtcgcagggt tct                                               23

<210> SEQ ID NO 4
<211> LENGTH: 22
<212> TYPE: DNA
<213> ORGANISM: Escherichia coli

<400> SEQUENCE: 4
aaagggctgt cgcagggttc tg                                                22

<210> SEQ ID NO 5
<211> LENGTH: 22
<212> TYPE: DNA
<213> ORGANISM: Escherichia coli

<400> SEQUENCE: 5
gtaaagggct gtcgcagggt tc                                                22

<210> SEQ ID NO 6
<211> LENGTH: 21
<212> TYPE: DNA
<213> ORGANISM: Escherichia coli

<400> SEQUENCE: 6
aagggctgtc gcagggttct g                                                 21

<210> SEQ ID NO 7
<211> LENGTH: 21
<212> TYPE: DNA
<213> ORGANISM: Escherichia coli

<400> SEQUENCE: 7
gtaaagggct gtcgcagggt t                                                 21

<210> SEQ ID NO 8
<211> LENGTH: 20
<212> TYPE: DNA
<213> ORGANISM: Escherichia coli

```
<400> SEQUENCE: 8
agggctgtcg cagggttctg                                          20

<210> SEQ ID NO 9
<211> LENGTH: 20
<212> TYPE: DNA
<213> ORGANISM: Escherichia coli

<400> SEQUENCE: 9
gtaaagggct gtcgcagggt                                          20

<210> SEQ ID NO 10
<211> LENGTH: 19
<212> TYPE: DNA
<213> ORGANISM: Escherichia coli

<400> SEQUENCE: 10
gggctgtcgc agggttctg                                           19

<210> SEQ ID NO 11
<211> LENGTH: 19
<212> TYPE: DNA
<213> ORGANISM: Escherichia coli

<400> SEQUENCE: 11
gtaaagggct gtcgcaggg                                           19

<210> SEQ ID NO 12
<211> LENGTH: 18
<212> TYPE: DNA
<213> ORGANISM: Escherichia coli

<400> SEQUENCE: 12
ggctgtcgca gggttctg                                            18

<210> SEQ ID NO 13
<211> LENGTH: 18
<212> TYPE: DNA
<213> ORGANISM: Escherichia coli

<400> SEQUENCE: 13
gtaaagggct gtcgcagg                                            18

<210> SEQ ID NO 14
<211> LENGTH: 24
<212> TYPE: DNA
<213> ORGANISM: Escherichia coli

<400> SEQUENCE: 14
tgccgttgtc gttatcccag ttga                                     24

<210> SEQ ID NO 15
<211> LENGTH: 23
<212> TYPE: DNA
<213> ORGANISM: Escherichia coli

<400> SEQUENCE: 15
gccgttgtcg ttatcccagt tga                                      23

<210> SEQ ID NO 16
<211> LENGTH: 23
<212> TYPE: DNA
```

```
<213> ORGANISM: Escherichia coli

<400> SEQUENCE: 16
tgccgttgtc gttatcccag ttg                                    23

<210> SEQ ID NO 17
<211> LENGTH: 22
<212> TYPE: DNA
<213> ORGANISM: Escherichia coli

<400> SEQUENCE: 17
ccgttgtcgt tatcccagtt ga                                     22

<210> SEQ ID NO 18
<211> LENGTH: 22
<212> TYPE: DNA
<213> ORGANISM: Escherichia coli

<400> SEQUENCE: 18
tgccgttgtc gttatcccag tt                                     22

<210> SEQ ID NO 19
<211> LENGTH: 21
<212> TYPE: DNA
<213> ORGANISM: Escherichia coli

<400> SEQUENCE: 19
cgttgtcgtt atcccagttg a                                      21

<210> SEQ ID NO 20
<211> LENGTH: 21
<212> TYPE: DNA
<213> ORGANISM: Escherichia coli

<400> SEQUENCE: 20
tgccgttgtc gttatcccag t                                      21

<210> SEQ ID NO 21
<211> LENGTH: 20
<212> TYPE: DNA
<213> ORGANISM: Escherichia coli

<400> SEQUENCE: 21
gttgtcgtta tcccagttga                                        20

<210> SEQ ID NO 22
<211> LENGTH: 20
<212> TYPE: DNA
<213> ORGANISM: Escherichia coli

<400> SEQUENCE: 22
tgccgttgtc gttatcccag                                        20

<210> SEQ ID NO 23
<211> LENGTH: 19
<212> TYPE: DNA
<213> ORGANISM: Escherichia coli

<400> SEQUENCE: 23
ttgtcgttat cccagttga                                         19

<210> SEQ ID NO 24
<211> LENGTH: 19
```

-continued

```
<212> TYPE: DNA
<213> ORGANISM: Escherichia coli

<400> SEQUENCE: 24
tgccgttgtc gttatccca                                              19

<210> SEQ ID NO 25
<211> LENGTH: 18
<212> TYPE: DNA
<213> ORGANISM: Escherichia coli

<400> SEQUENCE: 25
tgtcgttatc ccagttga                                               18

<210> SEQ ID NO 26
<211> LENGTH: 18
<212> TYPE: DNA
<213> ORGANISM: Escherichia coli

<400> SEQUENCE: 26
tgccgttgtc gttatccc                                               18

<210> SEQ ID NO 27
<211> LENGTH: 20
<212> TYPE: DNA
<213> ORGANISM: Enterococcus foecalis/Enterococcus faecium

<400> SEQUENCE: 27
gttcatcaaa ctgcttcact                                             20

<210> SEQ ID NO 28
<211> LENGTH: 19
<212> TYPE: DNA
<213> ORGANISM: Enterococcus faecalis/Enterococcus faecium

<400> SEQUENCE: 28
ttcatcaaac tgcttcact                                              19

<210> SEQ ID NO 29
<211> LENGTH: 19
<212> TYPE: DNA
<213> ORGANISM: Enterococcus faecalis/Enterococcus foecium

<400> SEQUENCE: 29
gttcatcaaa ctgcttcac                                              19

<210> SEQ ID NO 30
<211> LENGTH: 18
<212> TYPE: DNA
<213> ORGANISM: Enterococcus faecalis/Enterococcus faecium

<400> SEQUENCE: 30
tcatcaaact gcttcact                                               18

<210> SEQ ID NO 31
<211> LENGTH: 18
<212> TYPE: DNA
<213> ORGANISM: Enterococcus faecalis/Enterococcus faecium

<400> SEQUENCE: 31
gttcatcaaa ctgcttca                                               18

<210> SEQ ID NO 32
```

-continued

```
<211> LENGTH: 20
<212> TYPE: DNA
<213> ORGANISM: Enterococcus faecalis/Enterococcus faecium

<400> SEQUENCE: 32
aagatagcag gaggaatgac                                                    20

<210> SEQ ID NO 33
<211> LENGTH: 19
<212> TYPE: DNA
<213> ORGANISM: Enterococcus faecalis/Enterococcus faecium

<400> SEQUENCE: 33
agatagcagg aggaatgac                                                     19

<210> SEQ ID NO 34
<211> LENGTH: 19
<212> TYPE: DNA
<213> ORGANISM: Enterococcus faecalis/Enterococcus faecium

<400> SEQUENCE: 34
aagatagcag gaggaatga                                                     19

<210> SEQ ID NO 35
<211> LENGTH: 18
<212> TYPE: DNA
<213> ORGANISM: Enterococcus faecalis/Enterococcus faecium

<400> SEQUENCE: 35
gatagcagga ggaatgac                                                      18

<210> SEQ ID NO 36
<211> LENGTH: 18
<212> TYPE: DNA
<213> ORGANISM: Enterococcus faecalis/Enterococcus faecium

<400> SEQUENCE: 36
aagatagcag gaggaatg                                                      18

<210> SEQ ID NO 37
<211> LENGTH: 16
<212> TYPE: DNA
<213> ORGANISM: Artificial Sequence
<220> FEATURE:
<223> OTHER INFORMATION: Artificially synthesized.

<400> SEQUENCE: 37
aggaggtgaa accgca                                                        16

<210> SEQ ID NO 38
<211> LENGTH: 22
<212> TYPE: DNA
<213> ORGANISM: Artificial Sequence
<220> FEATURE:
<223> OTHER INFORMATION: Artificially synthesized.

<400> SEQUENCE: 38
ggttaagtcc cgcaacgagc gc                                                 22
```

METHOD FOR IDENTIFICATION OF THE INDICATORS OF CONTAMINATION IN LIQUID SAMPLES

CROSS REFERENCE TO RELATED APPLICATIONS

The present application claims the benefit of U.S. Provisional Application Ser. No. 60/149,365, filed Aug. 13, 1999, which is hereby incorporated herein by reference.

STATEMENT REGARDING FEDERALLY SPONSORED RESEARCH OR DEVELOPMENT

Not applicable

BACKGROUND OF THE INVENTION

The present invention relates generally to methods for the identification of microorganisms in liquid or liquified samples, and more particularly, but not by way of limitation, to methods using DNA for the identification of microorganisms which are indicators of contamination in liquid or liquified samples.

BRIEF DESCRIPTION OF THE ART

Most water-borne human pathogens cause infections and human disease via ingestion of fecal contaminated water or food. Various human parasites and pathogens are transmitted via human fecal contamination of water used for drinking, bathing, recreation, or washing/preparation of foods. To ensure good public health, there is a need for readily available methods to detect and enumerate pathogens in water.

While the presence of pathogens in water presents a significant public health concern, recovery of pathogens from environmental samples is generally difficult. Many fecal pathogens are infective at densities so low that water sample collection and concentration is inconvenient. Also, unpredictable physiological and morphological changes are observed in these pathogens in response to nutrient limitations and environmental stressors, and these injuries cause the organisms to exhibit atypical reactions and require specialized handling for their resuscitation. In addition, viable but unculturable organisms may be present in the water sample.

The methods commonly used to detect these pathogens were initially designed for clinical, rather than environmental, samples. However, clinical isolates are usually provided an ideal environment in which needed nutrients as well as protection from harsh environmental conditions, such as cold, heat, damaging chemicals and radiation, are readily supplied to the isolate. In contrast, environmental isolates are exposed to harsh, environmental conditions and effectively compete with organisms naturally present and adapted to life in the environment.

Pathogenic organisms are rarely readily adaptable to prolonged survival in the environment. For this reason, fecal microbial water contamination often is assessed by testing for harder and more robust, but not necessarily pathogenic, microbes, referred to as indicator organisms, such as the coliforms, especially *Escherichia coli*, and Enterococcus species. Indicator organisms serve to indicate whether a given water supply may be generally contaminated with fecal material without actually testing for the presence of all enteric pathogens. This contamination is viewed as predictive of the potential presence of enteric pathogens (i.e., without the presence of fecal material, the chances of these indicator organisms being present is usually remote).

Criteria for the establishment of the "ideal" indicator include the following factors: (1) the indicator should always be present in the presence of pathogens; (2) the indicator should always be present in a predictable ratio with pathogenic organisms; (3) the indicator should be specific for fecal contamination; (4) the indicator should be able to resist water treatment and disinfection processes to the same or a slightly greater extent than the pathogens; and (5) the indicator should be detectable by simple and rapid methods.

Although coliforms have historically served as the indicator bacteria for fecal contamination in United States water supplies, the term "coliform" encompasses four genera (Escherichia, Citrobacter, Enterobacter and Klebsiella) which include many species that are commonly found in the environment in the absence of fecal contamination. *E. coli* is the only species of coliform bacteria which is consistently and exclusively found in feces, and therefore, coliform detection methods are not specific for detecting fecal contamination in a water supply. Nonetheless, regulations based on detection and enumeration of "total coliforms" are still in effect in the United States.

Tests have also been developed to detect "fecal coliforms", a subgroup of total coliforms which are thermotolerant. However, this designation is also nonspecific, as it includes not only *E. coli,* but also various Klebsiella strains. Despite the fact that there are substantial environmental sources of Klebsiella, and this organism is infrequently found in human feces, the use of the designation "fecal coliform" as well as tests to identify these organisms remain routine.

Typically, fecal coliform identification has relied on methods for distinguishing phenotype aspects such as growth or motility characteristics, and for immunological and serological characteristics. Selective growth procedures and immunological methods are the traditional methods of choice for bacterial identification, and these can be effective for the presumptive detection of a large number of species within a particular genus. However, theses methods are time consuming and are subject to error.

Selective growth methods require culturing for one to several days in selective media, followed by subjective analysis, including various metabolic, biochemical and immunochemical tests to confirm the microbiological identities of the organisms. These methods are labor, time and supply intensive, and must be performed by an experienced investigator.

Immunological detection (e.g., ELISA) is more rapid and specific, however, it still requires growth of a significant population of organisms and isolation of the relevant antigens. The sensitivity levels of currently available ELISA tests are about $10^4$–$10^5$ organisms per milliliter, and organisms present at lower concentrations will not be detected; therefore, one or more culture steps are required in order to enrich the number of microorganisms present in the sample, and these culture steps are generally time-consuming. In addition, antigenic cross reactivity using these serological procedures can result in misidentification of organisms. Also, immunological detection typically does not distinguish living from dead cells.

Rapid processes for detecting fecal coliforms by growth in a medium containing a fluorogenic substrate (methylumbelliferyl galactoside) which is metabolized by the bacteria are described in U.S. Pat. No. 5,292,644 entitled "Rapid Process For Detecting Coliform Bacteria," and U.S. Pat. No. 5,518,894 entitled "Rapid Coliform Detection System." These processes are much less time intensive than the previously described methods, and the total amount of time required for a presence-absence result generally does not exceed seven hours.

Other methods rely on hydrolysis of methylumbelliferyl glucuronide by β-glucuronidase, such as the methods described in U.S. Pat. No. 5,429,933 entitled "Detection of First Generation Environmental Sourced Microbes in an Environmentally-Derived Sample." However, recent findings have shown that many coliform bacteria obtained from fecal samples do not possess β-glucuronidase, which is required to metabolize this fluorogenic substrate. Further, although 97% of clinical isolates of *E. coli* were β-glucuronidase-positive, only about 66–70% of all *E. coli* obtained from fecal samples were β-glucuronidase-positive. Therefore, these processes would fail to detect a significant portion, about 30%, of *E. coli* present in the fecal samples.

Therefore, interest has turned to detection of bacterial pathogens on the basis of specific DNA sequences. Colony hybridization uses a radiolabelled unique DNA gene probe fragment isolated from chromosomal DNA of the coliform of interest to identify colonies of the organism isolated from a water sample; this technique has higher sensitivity than those described above. Methods for hybridization of oligonucleotide probes to samples for detection of an organism or a group of organisms are described in U.S. Pat. No. 5,693,469 entitled "Nucleic Acid Probes and Methods for Detecting *Escherichia coli*," U.S. Pat. No. 5,792,854 entitled "Detection of Salmonella," and U.S. Pat. No. 5,795,717 entitled "Oligonucleotides for Detecting Bacteria and Detection Process." However, considerable time and expense is still required for hybridization methods, and a minimum of $10^3$–$10^4$ cells per milliliter are required for detection.

Another method of detection of bacterial pathogens on the basis of nucleic acid sequence involves DNA amplification and the use of the polymerase chain reaction (PCR). Theoretically, the presence of a single microorganism can be detected by this method. U.S. Pat. No. 5,652,102 entitled "Assay for Enterohemorrhagic *Escherichia coli* 0157:H7 by the Polymerase Chain Reaction" and U.S. Pat. No. 5,298,392 entitled "Process for Detection of Water-Borne Microbial Pathogens and Indicators of Human Fecal Contamination in Water Sample and Kits Therefor" both describe methods for detection of organisms by PCR and specific PCR primers for use in the methods. Patent '102 teaches the use of primers derived from the sequences of the genes encoding the Shiga-like toxins I and II, the eaeA gene which encodes an outer membrane protein, and the 60-MDa plasmid which is present in most enterohemorrhagic *E. coli* (EHEC) for the detection of the specific EHEC serotype 0157. Patent '392 teaches the use of primers derived from specific target genes for detection of groups of organisms; the target genes include the lacZ gene to detect all species from the genera Escherichia, Enterobacter, Citrobacter, and Klebsiella, the lamB gene to detect *E. coli* and all Salmonella and Shigella species, and the UidA gene to detect *E. coli, Shigella sonnei*, and *Shigella flexneri*. However, both of the methods described in '102 and '392 detect the amplification products by Southern blotting, which involves gel electrophoresis of the amplification products, transfer of the DNA to a membrane, and hybridization with a labeled primer specific for the amplification product and different from the primers used for amplification. This detection process is generally time consuming and expensive.

Thus, improved methods for detecting indicator organisms which are directly related to fecal contamination and/or the presence of pathogens which can cause waterborne disease which have reduced detection times and increased specificity and sensitivity of detection are being sought. It is to such methods, and primers used therein, that the present invention is directed.

SUMMARY OF THE INVENTION

According to the present invention, methods for the identification of bacteria in liquid or liquified samples as indicators of fecal contamination and/or the presence of pathogens which can cause waterborne disease are provided which avoid the disadvantages and defects of the prior art.

Broadly, species specific oligonucleotides based on the sequences of the *E. coli* specific lamB gene and the *Enterococcus faecalis/faecium* transposase gene Tn1546 are provided for detection and identification of these bacteria in a liquid or liquified sample.

The method of detection and identification preferably involves enrichment of the bacteria using selective culture media, recovery of bacteria from media, lysing of the bacteria to release DNA, polymerase chain reaction (PCR) amplification of the target sequences using the novel oligonucleotides, and specific detection of PCR products.

In particular, an object of the present invention is to provide novel oligonucleotides as primers for PCR assays for the specific detection and identification of *Enterococcus faecalis, Enterococcus faecium* and *Escherichia coli*.

Another object of the present invention, while achieving the before-stated object, is to provide PCR assay methods utilizing the novel primers.

Other objects, features and advantages of the present invention will become apparent from the following detailed description when read in conjunction with the appended claims.

DETAILED DESCRIPTION OF THE INVENTION

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of the invention.

The present invention provides a method for detecting water-borne microorganisms which serve as an indicator of the probable presence of pathogens, primarily of fecal origin. In a preferred embodiment, the method comprises the following steps: (1) providing a liquid or liquified sample (which may include treating the sample with a culture media to enrich microorganisms present in the sample); (2) recovering microorganisms from the treated sample; (3) lysing the recovered microorganisms to release substantially undegraded DNA therefrom; (4) providing specific primers which will hybridize to separated target strands of a target nucleotide sequence from the target gene of the microorganism of interest and amplify the target nucleotide sequence but not sequences found in other organisms; (5) mixing the primers with the recovered DNA; (6) amplifying the specific target nucleotide sequence with polymerase thereby extending the primers to make fully double-stranded replicas of the target DNA sequence; (7) detecting the presence of the amplicon (amplified target DNA sequence) by binding the amplicon to a microtiter plate and staining with a stain such as PICOGREEN, which selectively stains double stranded DNA; and (8) making a determination about the presence or absence of the microorganism in the original liquid or liquified sample based on presence or absence of the amplicon. Examples of the primers which may be used, and which are discussed in more detail below, are shown in Tables I, and II, III and IV.

TABLE I

LamK U Primer Sequences

| SEQ ID NO: | BASE SEQUENCE |
|---|---|
| 1 | gtaaagggctgtcgcagggttctg |
| 2 | taaagggctgtcgcagggttctg |
| 4 | aaagggctgtcgcagggttctg |
| 6 | aagggctgtcgcagggttctg |
| 8 | agggctgtcgcagggttctg |
| 10 | gggctgtcgcagggttctg |
| 12 | ggctgtcgcagggttctg |
| 3 | gtaaagggctgtcgcagggttct |
| 5 | gtaaagggctgtcgcagggttc |
| 7 | gtaaagggctgtcgcagggtt |
| 9 | gtaaagggctgtcgcagggt |
| 11 | gtaaagggctgtcgcaggg |
| 13 | gtaaagggctgtcgcagg |

TABLE II

LamK L Primer Sequences

| SEQ ID NO: | BASE SEQUENCE |
|---|---|
| 14 | tgccgttgtcgttatcccagttga |
| 15 | gccgttgtcgttatcccagttga |
| 17 | ccgttgtcgttatcccagttga |
| 19 | cgttgtcgttatcccagttga |
| 21 | gttgtcgttatcccagttga |
| 23 | ttgtcgttatcccagttga |
| 25 | tgtcgttatcccagttga |
| 16 | tgccgttgtcgttatcccagttg |
| 18 | tgccgttgtcgttatcccagtt |
| 20 | tgccgttgtcgttatcccagt |
| 22 | tgccgttgtcgttatcccag |
| 24 | tgccgttgtcgttatccca |
| 26 | tgccgttgtcgttatccc |

TABLE III

Entero U Primer Sequences

| SEQ ID NO: | BASE SEQUENCE |
|---|---|
| 27 | gttcatcaaactgcttcact |
| 28 | ttcatcaaactgcttcact |
| 30 | tcatcaaactgcttcact |
| 29 | gttcatcaaactgcttcac |
| 31 | gttcatcaaactgcttca |

TABLE IV

Entero L Primer Sequences

| SEQ ID NO: | BASE SEQUENCE |
|---|---|
| 32 | aagatagcaggaggaatgac |
| 33 | agatagcaggaggaatgac |
| 35 | gatagcaggaggaatgac |
| 34 | aagatagcaggaggaatga |
| 36 | aagatagcaggaggaatg |

In one embodiment of the present invention, the desired method of detecting bacteria in a liquid or liquified sample by PCR comprises providing a liquid or liquified sample suspected of containing bacteria, recovering said bacteria from the liquid or liquified sample, and lysing the bacteria to provide a DNA sample. A target gene and a target DNA sequence in the target gene are selected, and the DNA sample is incubated under amplification conditions with DNA polymerase and a primer pair for the target DNA sequence. The presence of amplified DNA indicates the presence of bacteria carrying the selected target DNA sequence. The target gene may be the lamB gene to detect the presence of *Escherichia coli,* or the target gene may be the transposase gene Tn1546 to detect the presence of *Enterococcus faecalis* and/or *Enterococcus faecium.*

In another embodiment, the desired method of detecting bacteria in a liquid or liquified sample by PCR comprises providing a liquid or liquified sample suspected of containing bacteria, recovering said bacteria from the liquid or liquified sample, and lysing the bacteria to provide a DNA sample. A pair of target genes and a target DNA sequence in each target gene are selected, and the DNA sample is incubated under amplification conditions with DNA polymerase and a primer pair for amplifying each target DNA sequence. The presence of amplified DNA indicates the presence of bacteria carrying the selected target DNA sequences. The target genes comprise the lamB gene to detect the presence of *E. coli* and the transposase gene Tn1546 to detect the presence of *Enterococcus faecalis* and/or *Enterococcus faecium.*

The term "liquid or liquified sample" may be used herein interchangeably with the term "test sample". The liquid or liquified sample may comprise sewage, sludge, soil, food, feed, and water. It is therefore contemplated that the liquid or liquified sample comprise any number of sample types, both environmental and clinical. Examples of the liquid or liquified sample include but are not limited to drinking water, bathing water, cerebrospinal fluid, blood, juices, soft drinks, wine or other alcoholic beverages, milk, milk products, cheeses, and yogurt.

The Polymerase Chain Reaction (PCR) is a method well known by persons of ordinary skill in the art and is described in U.S. Pat. No. 4,683,202, entitled "Process For Amplifying Nucleic Acid Sequences", issued Jul. 28, 1987 to K. Mullis, which is hereby expressly incorporated herein by reference. PCR is an effective procedure for generating large quantities of a target DNA sequence in vitro such that the target DNA sequences can be detected even when they are present in very low concentrations in original test samples. Thus, the disadvantages and defects of the prior art, such as low specificity and sensitivity due to very low concentrations of pathogens or indicators, no detection of nonculturable pathogens or indicators, and considerable time, expense and expertise required for detection of pathogens or indicators, can be overcome by the use of a PCR-based method.

PCR requires two synthetic oligonucleotide primers that are complementary to regions on opposite strands that flank the target DNA sequence and that, after annealing to the template DNA, have their 3' hydroxyl ends oriented towards each other. A target DNA sequence ranging from about 100 base pairs (bp) to about 35,000 bp in length, and more preferably from about 100 bp to about 2,000 bp in length, is present in a DNA template and lies between the annealing positions of the pair of primers. A thermostable DNA polymerase which can preferably withstand temperatures of 95° C. or higher as well as the four deoxyribonucleotides are supplied in the reaction. The PCR reaction is typically carried out in an automated, programmable block heater which can cycle between various temperatures. The first step in a cycle, termed the denaturation step, involves denaturing the DNA template from double-stranded to single-stranded nucleic acids preferably at a high temperature, such as 95° C. In the second step, termed the annealing step, the block is cooled to 55° C., for example, at which temperature the pair of primers anneal to their complementary sequences in the template DNA. In the third step, termed the extension step, the temperature is raised to a temperature which is optimum for the catalytic function of the DNA polymerase, which is typically from about 70° C. to about 75° C., wherein DNA synthesis results in doubling of the number of copies of the target DNA sequence present in the reaction. The steps are repeated for about 25 to about 45 cycles, and for each cycle, the number of target DNA sequences doubles.

The target gene and target DNA sequence present in the target gene should be selected based on the absence of the gene in other organisms or on the difference of the primers to sequences of other organisms. Generally, the target DNA sequence should be absent in essentially all other organisms, or the primers should be significantly low in similarity to sequences found in other organisms such that only the target gene of interest will be amplified by the primers. However, primers can also be designed to efficiently amplify target sequences present in more than one organism, such as organisms in a specific species, genus or group.

In one aspect, the present invention comprises a novel primer set ("LamK") specific for *E. coli* which is based on the *E. coli* lambda receptor gene lamB (GenBank accession numbers M26131; M26187) (J. M. Clement et al., *A System for Genetic Analysis in Gene lamB: First Results with Lambda-Resistant Tight Mutants*, 133 Ann. Inst. Pasteur Microbiol. 9–20 (1982)).

In a preferred embodiment, for detection of *E. coli*, the LamK primer set is SEQ ID NO:1 and SEQ ID NO:14. In alternative embodiments, the LamK primer set may comprise pairwise sets of 23- to 18-base corresponding subportions of each of SEQ ID NO:1 and SEQ ID NO:14. For example, the LamK primer set may comprise 23-base SEQ ID NO:2 and SEQ ID NO:15 or SEQ ID NO:3 and SEQ ID NO:16. Other examples of possible primer pairs for detection of *E. coli* are shown in Table V. The primers have been used to generate a 180-bp amplification product.

TABLE V

LamK Primer Pairs For Use In Detection Of *E. coli*
LamK Primer Sets

| Primer Size (No. of Bases) | LamK U Primer SEQ ID NO: | LamK L Primer SEQ ID NO: |
|---|---|---|
| 24 | 1 | 14 |
| 23 | 2 | 15 |
| 23 | 3 | 16 |
| 22 | 4 | 17 |
| 22 | 5 | 18 |
| 21 | 6 | 19 |
| 21 | 7 | 20 |
| 20 | 8 | 21 |
| 20 | 9 | 22 |
| 19 | 10 | 23 |
| 19 | 11 | 24 |
| 18 | 12 | 25 |
| 18 | 13 | 26 |

The LamK primer set described herein has been tested with other microorganisms as templates. No amplification product was identified with the following bacteria when using a primer set comprising SEQ ID NO:1 and SEQ ID NO:14, *Shigella boydii, Shigella flexneri, Salmonella typhi,* *Salmonella enterica, Salmonella arizonae, Enterobacter cloacae, Enterobacter aeromonas, Enterococcus faecalis, Enterococcus faecium, Streptococcus pyogenes,* Pseudomonas species, *Aeromonas hydrophila,* Acinetobacter species, *Klebsiella pneumoniae, Listeria monocytogenes, Neisseria meningitidis, Campylobacter jejuni, Campylobacter coli,* Erwinia species, and *Citrobacter freundii.*

In another aspect, the present invention comprises a novel primer set ("Entero") specific for Enterococcus which is based on the transposase gene Tn1546. of *Enterococcus faecium* (GenBank accession number AF093508) (L. B. Jensen, *Internal Size Variations in Tn1546-Like Elements Due to the Presence of IS1216V*, 169 FEMS Microbiol. Lett. 348–354 (1998)).

In a preferred embodiment for detection of *Enterococcus faecalis* or *Enterococcus faecium,* the Entero primer set is SEQ ID NO:27 (Etero U) and corresponding SEQ ID NO:32 (Entero L). In an alternative embodiment, the Entero primer set may comprise pairwise sets of 19- or 18-base corresponding subportions of each of SEQ ID NO:27 and SEQ ID NO:32. For example, the Entero primer set may comprise 18-base SEQ ID NO:30 and SEQ ID NO:35 or SEQ ID NO:31 and SEQ ID NO:36. Other examples of possible primer pairs for detection of *Enterococcus faecalis* or *E. faecium* are shown in Table VI.

TABLE VI

Entero Primer Pairs For Use In Detection Of *Enterococcus faecalis* and *E. faecium*
ENTERO PRIMER SETS

| Primer Size (No of Bases) | Entero U Primer (SEQ ID NO:) | Entero L Primer (SEQ ID NO:) |
|---|---|---|
| 20 | 27 | 32 |
| 19 | 28 | 33 |
| 19 | 29 | 34 |
| 18 | 30 | 35 |
| 18 | 31 | 36 |

The Entero primers have been used to generate an amplification product from of about 450 bp from *Enterococcus faecium* and *Enterococcus faecalis.*

The Entero primer set described herein has been tested with other microorganisms as templates. No amplification product was identified with the following bacterial strains when using a primer set comprising SEQ ID NO:27 and SEQ ID NO:32, *Shigella boydii, Shigella flexneri, Salmonella typhi, Salmonella enterica, Salmonella arizonae, Enterobacter cloacae, Enterobacter aeromonas, Escherichia coli, Streptococcus pyogenes,* Pseudomonas species, *Aeromonas hydrophila,* Acinetobacter species, *Klebsiella pneumoniae, Listeria monocytogenes, Neisseria meningitidis, Campylobacter jejuni, Campylobacter coli,* Erwinia species, *Hafnia alvei* and *Citrobacter freundii.*

A third primer set used as a control and referred to herein as the General primer set, is based on the 16S RNA gene (J. Clinical Microbiol. 32: 335–351 (1994)). The General primers are designated as DG74 and PL06. It is well known that nucleic acid sequences associated with the ribosomes of bacteria are often highly conserved across genera. For example, Lane et al (WO 9015157) teach universal nucleic acid probes that hybridize to conserved regions of 23S or 16S rRNA of eubacteria. Because the 16S rRNA gene is highly conserved between bacterial species, the General primer set is used as a positive control to generate an amplification product from several bacterial species, including *E. coli, E. faecalis* and *E. faecium,* which may be present in the test sample. The General primer set therefore is used as a control for determining the quality of the DNA sample prepared from each liquid or liquified sample. Primer DG74 has the sequence SEQ ID NO:37 (AGGAGGTGAAACCGCA) and primer PL06 has the sequence SEQ ID NO:38 (GGTTAAGTCCCGCAACGAGCGC).

Effective LamK primers may include not only the primers having base sequences SEQ ID NO:1–SEQ ID NO:26, but also may include primers having sequences of 25–40 bases, inclusive, which comprise at least one of the sequences represented by SEQ ID NO:1–SEQ ID NO:26, respectively.

Effective Entero primers may include not only the primers having base sequences of SEQ ID NO:27–SEQ ID NO:36, but also may include primers having sequences of 21–40 bases, inclusive, which comprise at least one of the sequences represented by SEQ ID NO:27–SEQ ID NO:36, respectively.

More specifically, the present invention contemplates an oligonucleotide primer, or a method which uses it in detecting *E. coli,* wherein the oligonucleotide primer has 18–40 bases, inclusive, wherein the bases at the 5' end comprise SEQ ID NOs:1, 3, 5, 7, 9, 11, 13, 14, 16, 18, 20, 22, 24, or 26. Further, the present invention contemplates an oligonucleotide primer or a method which uses it in detecting *E. coli,* wherein the oligonucleotide primer has 18–40 bases, inclusive, wherein the bases at the 3' end comprise SEQ ID NOs:1, 2, 4, 6, 8, 10, 12, 14, 15, 17, 19, 21, 23, or 25.

Further, the present invention contemplates an oligonucleotide primer, or a method which uses it in detecting *Enterococcus faecalis* of *Enterococcus faecium,* wherein the oligonucleotide primer has 18–40 bases, inclusive wherein the bases at the 5' end comprise SEQ ID NOs: 27, 29, 31, 32, 34, or 36. Further, the present invention contemplates an oligonucleotide primer or a method which uses it in detecting *Enterococcus faecalis* or *Enterococcus faecium,* wherein the oligonucleotide primer has 18–40 bases, inclusive, wherein the bases at the 3' end comprise SEQ ID Nos: 27, 28, 30, 32, 34, or 36.

Where used herein, the term "inclusive" is intended to mean that each base corresponding to a numeral within the stated range, and the extremes of the range, are explicitly contemplated as included in the claimed invention.

For the detection method used as described hereinafter, preferably, one of the primers in each primer set that is used is biotinylated. The present invention is not limited to this method and persons of ordinary skill in the art will readily be aware of alternative methods of using the primers described herein and optimal process conditions. The use of biotin as a chemical label for DNA probes, as well as the method of biotinylating an oligonucleotide, are well known to persons of ordinary skill in the art, and therefore it is not necessary that they be discussed further herein.

In one embodiment, the desired method of detecting microorganisms in a liquid or liquified sample by PCR comprises providing a liquid or liquified sample desired to be tested for the presence of *E. coli* bacteria, recovering said bacteria from the liquid or liquified sample, and lysing the bacteria to provide a DNA sample. The DNA sample is then treated under amplification conditions with at least one of the LamK primer sets comprising a pair of primers described herein. The presence of amplified DNA (an amplicon) in excess of a threshold amount indicates the presence of *E. coli* in the liquid or liquified sample.

In another embodiment, the desired method of detecting microorganisms in a liquid or liquified sample by PCR comprises providing a liquid or liquified sample desired to be tested for the presence of *Enterococcus faecalis* or *E. faecium* bacteria, recovering said bacteria from the liquid or liquified sample, and lysing the bacteria to provide a DNA sample. The DNA sample is then treated under amplification conditions with at least one of the Entero primer sets comprising a pair of primers described herein. The presence of amplified DNA (an amplicon) in excess of a threshold amount indicates the presence of *Enterococcus faecalis* and/or *Enterococcus faecium* in the liquid or liquified sample.

In the first step of one version of the method of the present invention, a 10 ml portion of the liquid or liquified sample (as defined elsewhere) herein which is desired to be tested for bacteria is mixed with 10 ml of an enrichment media for enhancing growth of bacteria which may be present in the sample and is incubated, preferably at 41°–44° C. for three to five hours. In one aspect, the enrichment media used is concentrated coliform-specific media based on metabolism by bacteria of the fluorogenic substrate 4-methylumbelliferyl-β-D-galactoside (MUGal) by β-galactosidase, which has previously been used for detection of coliforms such as *E. coli* (see Table VII). Hydrolysis of MUGal results in a measurable fluorescent by-product, 4-methylumbelliferone (MU), which can be detected via known methods such as described in U.S. Pat. No. 5,518, 894, which is expressly incorporated herein by reference in its entirety.

TABLE VII

COLIFAST ™ Media

| Ingredients | amount/366 g | (g) % | g/500 ml |
|---|---|---|---|
| Proteose Peptone No. 3 | 75.00 | 20.49 | 2.66 |
| Yeast Extract | 45.00 | 12.30 | 1.60 |
| NaCl | 225.00 | 61.48 | 8.00 |
| Pyruvate | 6.00 | 1.64 | 0.20 |
| Sodium Lauryl Sulphate | 6.00 | 1.64 | 0.20 |
| Bile Salts | 3.00 | 0.82 | 0.10 |
| IPTG | 3.00 | 0.82 | 0.10 |
| MUGal | 3.00 | 0.82 | 0.10 |
| Lactose | 0.0001 | 0.00003 | 0.10 |

Following the incubation period, the bacteria present in the test sample are recovered and lysed to isolate DNA for use as a DNA template for PCR. Methods of DNA isolation from bacteria are well known to persons of ordinary skill in the art. For example, kits which provide rapid and simple isolation of DNA are available from many companies which provide molecular biology products, such as Bio-Rad, Qiagen, Life Technologies and Promega. Therefore, it will be understood the present invention is not limited to the method of DNA isolation described herein. The method described herein is provided for example only, and other methods of DNA isolation are considered to be within the scope of the present invention.

In the method of DNA isolation described herein by purpose of example, about 0.5 ml to about 2.5 ml of the sample enriched in a media described herein is collected and centrifuged at 10,000 g or higher for 4 minutes, forming a pellet. The supernatant is carefully removed, and the pellet remaining is washed again in an optional step by adding 1 ml of sterile water and mixing with a pipette. The optional step is preferred if the sample is suspected of containing substances which may inhibit the PCR reaction. The sample is then again centrifuged at 10,000 g or higher for 4 minutes.

The supernatant is again carefully removed. The pellet remaining is then dissolved in 40 µl sterile water and boiled for 10 minutes to lyse the bacteria and release substantially undegraded DNA from the organisms, resulting in a DNA sample prepared from the liquid or liquified sample. Upon briefly centrifuging the DNA sample to concentrate any liquid which may have evaporated during the boiling step, the DNA sample is ready for PCR amplification with the primer sets described in detail previously.

In one embodiment, a microtiter plate is used in the amplification step, and to each well is added 10 µl of DNA sample as prepared immediately above. Each well also includes 40 µl of a premix of a PCR reaction buffer, which includes 5 µl of PCR buffer, 0.2 µl of thermostable DNA polymerase, 1 µl of each dNTP, 0.5 µl of each primer and 32.8 µl of sterile water. The final concentrations in the 50 µl PCR reaction are as follows: 10 mM Tris-HCl, pH 8.8, 1.5 mM $MgCl_2$, 50 mM KCl, 0.1% Triton X-100, 0.2 units of thermostable DNA polymerase (e.g., Dynazyme™ from Finzyme or Taq polymerase used at a higher concentration), 200 µM of each dNTP, and 50 pmol of each primer.

Each DNA sample is added to three separate wells: the first well contains the General primer set, the second well contains a LamK primer set, and the third well contains an Entero primer set.

In addition to the DNA sample wells, it is preferred that a number of performance and assay control wells are used to optimize the results obtained and to identify false negatives or false positives. Listed in Table VIII are examples of control wells which can be used on the microtiter plate in addition to the sample wells.

For example, a control designated in Table VIII as "G(neg control)" is performed in a well using a PCR premix with DNA polymerase, the General primer set, and no DNA template. The expected result is negative; a positive result would indicate contamination of the reagents by DNA. A control designated in Table VIII as "L(neg control)" is performed in a well using a PCR premix with DNA polymerase, a LamK primer set, and no DNA template. The expected result is negative; a positive result would indicate contamination of the reagents by DNA. A control designated in Table VIII as ("E (neg control)" is performed in a well using a PCR premix with DNA polymerase, an Entero primer set, and no DNA template. The expected result is negative; a positive result would indicate contamination of the reagents by DNA.

A control designated in Table VIII as "Bact (pos control)" is performed in a well using a PCR premix with DNA polymerase, the General primer set, and a quantity of any bacterial DNA (for example, *E. coli*). The expected result is positive; a negative result would indicate a problem or problems with the reagents, primers, and/or process. A control designated in Table VIII as "*E. coli* (std)" is performed in a well using a PCR premix with DNA polymerase, a LamK primer set, and a known or standard quantity of *E. coli* DNA. The expected result is positive; a negative result would indicate a problem or problems with the reagents, primers, and/or process.

Finally, a control designated in Table VIII as "Sample (pos control)" is performed in a well using a PCR premix with DNA polymerase, the General primer set, and unknown DNA from each sample. The expected result is positive (unless the sample is expected to be sterile). A negative result would indicate that PCR inhibitors were in the sample, indicating that additional pre-PCR processing may be necessary.

After all reagents are added to the microtiter plate, a film is placed over the microtiter plate to prevent evaporation of water and to concentrate all reagents together in each well to ensure accurate interactions between the reagents. Such films are known in the art and include, but are not limited to, films produced by Perkin-Elmer Corporation.

In the PCR amplification step of the method of the present invention, the amplification is performed in one version in a thermal cycler, such as the Genius thermal cycler (Techne, Incorporated), and after a 94° C.±1° C., 30 second incubation to completely denature all DNA present, the reaction mixture is repeatedly cycled between 95° C. for 5 seconds, then 60° C.±1° C. for 10 seconds, followed by 72° C. for 20 seconds. The cycle is repeated 40 times, then allowed a final extension incubation at 72° C. for one minute. This protocol and the temperatures may be modified to optimize performance with the various primer set described herein.

TABLE VIII

Control Wells for PCR Amplification

| Control Name | Primer Set | DNA Template | Expected Results | Purpose for Control | Incorrect Result and Interpretation |
|---|---|---|---|---|---|
| G (neg control) | General | None | Neg | Check for false positive | Positive indicates DNA contamination of reagents |
| L (neg control) | LamK | None | Neg | Check for false positive | Positive indicates DNA contamination of reagents |
| E (neg control) | Entero | None | Neg | Check for false positive | Positive indicates DNA contamination of reagents |
| Bact (pos control) | General | Any bacterial DNA | Pos | Check for false negatives | Negative indicates problems with reagents, primers or process |
| E. coli (std) | LamK | Std. Quantity of E. coli DNA | Pos | Check for false negatives, and semi-quantification | Negative result indicates problems with reagents, primers or process; known amount of E. coli DNA can be used for semi-quantification |
| Ent (std) | Entero | Std. Quantity of E. faecalis/ faecium | Pos | Check for false negatives, and semi-quantification | Negative result indicates problems with reagents, primers or process; known amount of E. coli |
| Sample (pos control) | General | Unknown sample DNA | Pos | Check for false negatives of sample | Negative result indicates PCR inhibitors in the sample |

In a detection step, following the amplification step, a 50 µl portion of the incubated mixture in each well is applied to a detection well on a second microtiter plate which is coated with streptavidin, to which the biotin present on one primer of each primer set selectively binds.

The plate is incubated at room temperature for ten minutes with shaking. The supernatant is carefully removed. Each well is washed twice; a washing step includes adding 100 µl of sterile water, brief shaking, and careful removal of the supernatant. Then 100 µl of sterile distilled water is added to each well, and 1 µl of a detection reagent is added to each well and incubated at room temperature for one minute before transferring the microtiter plate to a fluorescence reader, where the results are determined using an excitation wavelength in the range of from about 480 nm to about 500 nm and an emission wavelength in the range of from about 520 nm to about 530 nm. The presence of amplicons bound to the streptavidin on the second microtiter plate is detected by the detection reagent.

In a preferred version, the detection reagent is the substrate PICOGREEN. The use of PICOGREEN as a stain for double stranded DNA (dsDNA) is described in U.S. Pat. No. 5,824,557 entitled, "Method for Detecting and Quantitating Nucleic Acid Impurities in Biochemical Preparations", issued Oct. 20, 1998 to T. J. Burke et al and assigned to PanVera Corporation, which is hereby expressly incorporated herein by reference. PICOGREEN is an ultra sensitive fluorescent nucleic acid stain which is ideal for quantitating dsDNA in the microtiter plate format. The ability of this reagent to detect very small amounts of dsDNA in the presence of contaminating RNA, single stranded DNA (ssDNA) or proteins, combined with its wide linear response, provides significant advantages over other methods.

Free PICOGREEN dye is essentially nonfluorescent and exhibits a greater than 1,000-fold fluorescence enhancement upon binding to dsDNA. PICOGREEN staining is highly selective for dsDNA over RNA, ssDNA and oligonucleotides, and is not compromised by the presence of proteins, nucleotides and other sample contaminants in the reaction.

However, it will be understood by a person of ordinary skill in the art that although PICOGREEN is a preferred stain, other detection reagents, including other dsDNA stains well known to persons of ordinary skill in the art, may be used in the present invention.

The detection reagent controls which contain only PICOGREEN(or other detection reagent) and each of the primer sets are used to determine a baseline fluorescence for determining presence or absence of *E. coli* and/or *Enterococcus faecalis/faecium*.

In a preferred version, a sample is considered to contain *E. coli* if the sample fluorsecence equals or exceeds a threshold which is twice the fluorescence of the detection reagent control which contained the LamK primer set. In another preferred version, a sample is considered to contain *Enterococcus faecalis* and/or *E. faecium* if the sample fluorescence equals or exceeds a threshold which is twice the fluorescence of the detection reagent control which contains the Entero primer set. Other thresholds may be chosen if a lesser or greater degree of confidence in the presence/absence decision is desired.

If a positive sample well containing either the *E. coli* primer set or the Enterococcus primer set is seen, the corresponding sample well containing the General primer set must be positive, or the result is invalid. However, when the sample well containing the General primer set is positive and the other two sample wells negative, this result indicates that bacteria other than *E. coli, E. faecalis* or *E. faecium* are present.

The detection method as described in detail herein is designed to detect the presence or absence of the indicator organism. However, a semiquantitative result can also be obtained using a similar method. In this method, to a series of wells is added increasing known amounts of *E. coli* or Enterococcus so that a standard curve can be constructed. The result obtained from the DNA sample collected from a liquid or liquified sample can be directly compared to the standard curve to determine the approximate amount of indicator organism present in the liquid or liquified sample. The use of PICOGREEN or other detection reagents will allow for quantitation of the dsDNA present, and the assay will display a linear correlation between dsDNA concentration and fluorescence, allowing a detection range extending from about 25 pg/ml to about 1 µg/ml dsDNA using a single PICOGREEN dye concentration.

Any of the components used in the method described herein, including the primers, the detection wells, and the detection reagents, may be packaged in a kit for use in a method for detecting *E. coli* and/or *Enterococcus faecalis* and *Enterococcus faecium*.

In one embodiment, a desired kit for use in a method for detecting *Escherichia coli* in a liquid or liquified sample comprises a primer set for amplification of a sequence in the lamB gene. The primer set is selected from the primer sets described in Table V or elsewhere herein such as primer sequences of up to 40 bp comprising SEQ ID NO:1 and SEQ ID NO:14. One of the two primer sequences of the primer set provided in the kit will be biotinylated. The kit may also include a detection reagent, such as PICOGREEN, for detection of an amplified sequence in the lamB gene, and a detection well having streptavidin coated thereon wherein the amplified sequence is detected by the detection reagent.

In another embodiment, a desired kit for use in a method for detecting *Enterococcus faecalis* and/or *Enterococcus faecium* in a liquid or liquified sample comprises a primer set for amplification of a sequence in the transposase gene Tn1546. The primer set is selected from the primer sets described in Table VI or elsewhere herein such as primer sequences of up to 40 bp comprising SEQ ID NO:27 and SEQ ID NO:32. One of the two primer sequences provided in the kit will be biotinylated. The kit may also include a detection reagent, such as PICOGREEN, for detection of an amplified sequence in the transposase gene Tn1546, and a detection well having streptavidin coated thereon wherein the amplified sequence is detected by the detection reagent. As noted above, kits may comprise primer sets for both *E. coli* and *Enterococcus faecalis/faecium* and may further comprise more than one primer set appropriate for each species of bacteria.

From the above description, it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit and scope of the invention disclosed and as defined in the appended claims.

What is claimed is:

1. An oligonucleotide primer having up to 40 bases and comprising the sequence SEQ ID NO:1; or SEQ ID NO:14 wherein the primer is specific for the detection of *E. coli*.

2. An oligonucleotide primer having 23–40 bases and comprising SEQ ID NO:2; or SEQ ID NO:3 wherein the primer is specific for the detection of *E. coli*.

3. An oligonucleotide primer having 23–40 bases and comprising SEQ ID NO:15; or SEQ ID NO:16 wherein the primer is specific for the detection of *E. coli*.

4. A method of specifically detecting *E. coli* in a liquid or liquified sample by polymerase chain reaction, comprising:

providing a liquid or liquified sample;

recovering bacteria from the liquid or liquified sample;

lysing the bacteria to provide a DNA sample;

treating the DNA sample under PCR conditions with a primer set specific for *E. coli* for forming an amplified DNA wherein the primer set comprises SEQ ID NO:1 and SEQ ID NO:14; and detecting the presence of amplified DNA as an indication of the presence of *E. coli* in the liquid or liquified sample.

5. The method of claim 4 wherein in the step of detecting the presence of amplified DNA, the presence of *Escherichia coli* is indicated when a signal is obtained which exceeds a predetermined threshold.

6. A method of specifically detecting *E. coli* in a liquid or liquified sample by polymerase chain reaction, comprising:

providing a liquid or liquified sample;

recovering bacteria from the liquid or liquified sample;

lysing the bacteria to provide a DNA sample;

selecting a target gene of *E. coli* and selecting an *E. coli*-specific target DNA sequence in the target gene;

incubating the DNA sample under amplification conditions with a DNA polymerase and a primer pair specific for *E. coli* for amplifying the target DNA sequence; and detecting the presence of amplified DNA as a specific indication of the presence of *E. coli* carrying the selected *E. coli*-specific target DNA sequence, wherein the target gene is the lamB gene of *Escherichia coli*.

7. A kit for use in specifically detecting *Escherichia coli* in a liquid or liquified sample, the kit comprising a primer pair having a first primer comprising SEQ ID NO: 1 and a second primer comprising SEQ ID NO: 14.

8. The kit of claim 7 further comprising a detection agent for detection of amplified DNA produced using the primer pair under amplification conditions.

9. The kit of claim 8 wherein the detection reagent is a dsDNA stain.

10. The kit of claim 8 further comprising a detection well having streptavidin coated thereon wherein the amplified DNA sequence is detected by the detection reagent.

11. The kit of claim 7 wherein the first primer or the second primer is biotinylated.

12. A method of specifically detecting *E. coli* in a liquid or liquified sample by polymerase chain reaction, comprising:

providing a liquid or liquified sample;

recovering bacteria from the liquid or liquified sample;

lysing the bacteria to provide a DNA sample;

treating the DNA sample under PCR conditions with a primer set specific for *E. coli* for forming an amplified DNA wherein the primer set comprises SEQ ID NO:2 and SEQ ID NO:15; and detecting the presence of amplified DNA as an indication of the presence of *E. coli* in the liquid or liquified sample.

13. The method of claim 12 wherein in the step of detecting the presence of amplified DNA, the presence of *Escherichia coli* is indicated when a signal is obtained which exceeds a predetermined threshold.

14. A method of specifically detecting *E. coli* in a liquid or liquified sample by polymerase chain reaction, comprising:

providing a liquid or liquified sample;

recovering bacteria from the liquid or liquified sample;

lysing the bacteria to provide a DNA sample;

treating the DNA sample under PCR conditions with a primer set specific for *E. coli* for forming an amplified DNA wherein the primer set comprises SEQ ID NO:3 and SEQ ID NO:16; and detecting the presence of amplified DNA as an indication of the presence of *E. coli* in the liquid or liquified sample.

15. The method of claim 14 wherein in the step of detecting the presence of amplified DNA, the presence of *Escherichia coli* is indicated when a signal is obtained which exceeds a predetermined threshold.

16. A kit for use in detecting *Escherichia coli* in a liquid or liquified sample, the kit comprising a primer pair having a first primer comprising SEQ ID NO: 2, and a second primer comprising SEQ ID NO: 15.

17. The kit of claim 16 further comprising a detection agent for detection of the amplified DNA produced using the primer pair under amplification conditions.

18. The kit of claim 17 wherein the detection reagent is a dsDNA stain.

19. The kit of claim 17 further comprising a detection well having streptavidin coated thereon wherein the amplified DNA sequence is detected by the detection reagent.

20. The kit of claim 16 wherein the first primer and the second primer is biotinylated.

21. A kit for use in detecting *Escherichia coli* in a liquid or liquified sample, the kit comprising a primer pair having a first primer comprising SEQ ID NO: 3 and a second primer comprising SEQ ID NO: 16.

22. The kit of claim 21 further comprising a detection agent for detection of the amplified DNA produced using the primer pair under amplification conditions.

23. The kit of claim 22 wherein the detection reagent is a dsDNA stain.

24. The kit of claim 22 further comprising a detection well having streptavidin coated thereon wherein the amplified DNA sequence is detected by the detection reagent.

25. The kit of claim 21 wherein the first primer and the second primer is biotinylated.

* * * * *

UNITED STATES PATENT AND TRADEMARK OFFICE
CERTIFICATE OF CORRECTION

PATENT NO. : 6,723,505 B1 Page 1 of 2
APPLICATION NO. : 09/634960
DATED : April 20, 2004
INVENTOR(S) : Frank Karlsen It is certified that error appears in the above-identified patent and that said Letters Patent is hereby corrected as shown below:

Column 25, Line 11: After the word "of" and before the word "amplified" insert the word --said--.

Column 25, Line 15: After the word "of" and before the word "amplified" insert the word --said--.

Column 25, Line 18: After the word "E. Coli" insert the words --but not Shigella boydii, Shigella flexneri, Salmonella typhi, Salmonella enterica, Salmonella arizonae, Enterobacter cloacae, Enterobacter aeromonas, Enterococcus faecalis, Enterococcus faecium, Streptococcus pyogenes, Pseudomonas species, Aeromonas hydrophila, Acinetobacter species, Klebsiella pneumoniae, Listeria monocytogenes, Neisseria meningitidis, Campylobacter jejuni, Campylobacter coli, Erwinia species, and Citrobacter freundii--.

Column 25, Line 28: After the word "E. Coli" insert the words --but not Shigella boydii, Shigella flexneri, Salmonella typhi, Salmonella enterica, Salmonella arizonae, Enterobacter cloacae, Enterobacter aeromonas, Enterococcus faecalis, Enterococcus faecium, Streptococcus pyogenes, Pseudomonas species, Aeromonas hydrophila, Acinetobacter species, Klebsiella pneumoniae, Listeria monocytogenes, Neisseria meningitidis, Campylobacter jejuni, Campylobacter coli, Erwinia species, and Citrobacter freundii--.

Column 25, Line 40: After the word "detection" delete the word "reagent" and insert the word --agent--.

Column 25, Line 44: After the word "detection" delete the word "reagent" and insert the word --agent--.

Column 26, Line 1: After the word "of" and before the word "amplified" insert the word --said--.

Column 26, Line 5: After the word "of" and before the word "amplified" insert the word --said--.

Column 26, Line 20: After the word "of" and before the word "amplified" insert the word --said--.

Column 26, Line 24: After the word "of" and before the word "amplified" insert the word --said--.

UNITED STATES PATENT AND TRADEMARK OFFICE
CERTIFICATE OF CORRECTION

PATENT NO. : 6,723,505 B1
APPLICATION NO. : 09/634960
DATED : April 20, 2004
INVENTOR(S) : Frank Karlsen It is certified that error appears in the above-identified patent and that said Letters Patent is hereby corrected as shown below:

Column 26, Line 34: After the word "detection" delete the word "reagent" and insert the word --agent--.

Column 26, Line 38: After the word "detection" delete the word "reagent" and insert the word --agent--.

Column 26, Line 49: After the word "detection" delete the word "reagent" and insert the word --agent--.

Column 26, Line 53: After the word "detection" delete the word "reagent" and insert the word --agent--.

Signed and Sealed this

Twentieth Day of March, 2007

JON W. DUDAS
*Director of the United States Patent and Trademark Office*